United States Patent
Woo et al.

(10) Patent No.: US 12,409,200 B2
(45) Date of Patent: Sep. 9, 2025

(54) COMPOSITION FOR TREATING HAIR LOSS OR PROMOTING HAIR GROWTH COMPRISING MILK THISTLE FLOWER EXTRACT AS AN ACTIVE INGREDIENT

(71) Applicant: BioSpectrum, Inc., Yongin-si (KR)

(72) Inventors: Ji Eun Woo, Suwon-si (KR); Seoung Woo Shin, Seoul (KR); Eun Sun Jung, Suwon-si (KR); Deok Hoon Park, Seongnam-si (KR)

(73) Assignee: BIOSPECTRUM, INC., Yongin-si (KR)

( * ) Notice: Subject to any disclaimer, the term of this patent is extended or adjusted under 35 U.S.C. 154(b) by 1 day.

(21) Appl. No.: 18/013,343

(22) PCT Filed: Aug. 18, 2022

(86) PCT No.: PCT/KR2022/012362
§ 371 (c)(1),
(2) Date: Dec. 28, 2022

(87) PCT Pub. No.: WO2023/022540
PCT Pub. Date: Feb. 23, 2023

(65) Prior Publication Data
US 2024/0115642 A1    Apr. 11, 2024

(30) Foreign Application Priority Data
Aug. 18, 2021  (KR) .................. 10-2021-0108678

(51) Int. Cl.
| | |
|---|---|
| *A61K 36/28* | (2006.01) |
| *A61K 9/00* | (2006.01) |
| *A61K 9/06* | (2006.01) |
| *A61K 9/16* | (2006.01) |
| *A61K 9/20* | (2006.01) |
| *A61K 9/48* | (2006.01) |
| *A61K 47/10* | (2017.01) |
| *A61K 47/12* | (2006.01) |
| *A61K 47/18* | (2017.01) |
| *A61K 47/26* | (2006.01) |

(52) U.S. Cl.
CPC ............ *A61K 36/28* (2013.01); *A61K 9/0056* (2013.01); *A61K 9/06* (2013.01); *A61K 9/1623* (2013.01); *A61K 9/2013* (2013.01); *A61K 9/2018* (2013.01); *A61K 9/2059* (2013.01); *A61K 9/4858* (2013.01); *A61K 9/4866* (2013.01); *A61K 47/10* (2013.01); *A61K 47/12* (2013.01); *A61K 47/183* (2013.01); *A61K 47/186* (2013.01); *A61K 47/26* (2013.01); *A61K 2236/33* (2013.01); *A61K 2236/331* (2013.01); *A61K 2236/333* (2013.01)

(58) Field of Classification Search
CPC ...... A61K 36/28; A61K 9/0056; A61K 9/006; A61K 9/1623; A61K 9/2013; A61K 9/2018; A61K 9/2059; A61K 9/4858; A61K 9/4866; A61K 47/10; A61K 17/12; A61K 47/183; A61K 47/186; A61K 47/26; A61K 2236/33; A61K 2236/331; A61K 2236/333; A61K 33/105; A61K 8/9789; A61P 17/14; A61Q 7/00
See application file for complete search history.

(56) References Cited

FOREIGN PATENT DOCUMENTS

| KR | 10-2016-0115461 | 10/2016 |
|---|---|---|
| KR | 10-2016-0140417 | 12/2016 |

OTHER PUBLICATIONS

Kim et al. (KR102142930B1 Machine Translation) (Year: 2020).*
Edelgard (DE4323614A1 Machine Translation) (Year: 1995).*
Richard V. Clark et al., "Marked Suppression of Dihydrotestosterone in Men with Benign Prostatic Hyperplasia by Dutasteride, a Dual 5α-Reductase Inhibitor", The journal of clinical endocrinology & metabolism 89(5): 2179-2184, May 2004.
Ryan R. Driskell et al., "Hair follicle dermal papilla cells at a glance" Journal of Cell Science 124(8), 1179-1182, Apr. 2011.

(Continued)

*Primary Examiner* — Robert A Wax
*Assistant Examiner* — Quanglong N Truong
(74) *Attorney, Agent, or Firm* — LEX IP MEISTER, PLLC

(57) ABSTRACT

The present invention relates to a composition for preventing hair loss or promoting hair growth containing a milk thistle flower extract as an active ingredient. More specifically, the present invention relates to a cosmetic composition, pharmaceutical composition and food composition containing a milk thistle flower extract as an active ingredient, which are able to promote hair growth by inducing the proliferation of dermal papilla cells reduced due to senescence, and activate dermal papilla cells by inhibiting the senescence of dermal papilla cells through inhibition of the activity of senescence-associated β-galactosidase (SA-β-Gal) and the production of senescence-associated secretory phenotypes, thereby preventing hair loss or promoting hair.

The composition according to the present invention has no skin irritation and cytotoxicity, and thus has excellent safety for the human body, and at the same time, is very effective in promoting the proliferation of dermal papilla cells and inhibiting the senescence of dermal papilla cells. Thus, it may be useful as an active ingredient in a cosmetic composition, a pharmaceutical composition or a food composition for preventing hair loss or promoting hair growth.

5 Claims, 2 Drawing Sheets

(56) References Cited

OTHER PUBLICATIONS

Pietro Gentile et al., "Advances in Regenerative Stem Cell Therapy in Androgenic Alopecia and Hair Loss: Wnt Pathway, Growth-Factor, and Mesenchymal Stem Cell Signaling Impact Analysis on Cell Growth and Hair Follicle Development", Cells 2019, 8, 466, May 16, 2019.
Hye In Cheon et al., "Flavonoid Silibinin Increases Hair-Inductive Property Via Akt and Wnt/β-Catenin Signaling Activation in 3-Dimensional-Spheroid Cultured Human Dermal Papilla Cells", J. Microbiol. Biotechnol. (2019), 29(2), 321-329, Dec. 24, 2018.
Shigeki Inui et al., "Molecular basis of androgenetic alopecia: From androgen to paracrine mediators through dermal papilla", Journal of Dermatological Science 61 (2011): 1-6, Jan. 2011.
Jeon Yeon Lim et al., "The Recent Research Trend of Hair Loss Preventers (Hair Grower, Hair Growth Promoters, and Hair Tonics)", Kor. J. Aesthet. Cosmetol., vol. 12 No. 6, 773-786, Dec. 2014.
Mi Hee Kwack et al., "Minoxidil activates B-catenin pathway in human dermal papilla cells: A possible explanation for its anagen prolongation effect", Journal of Dermatological Science 62 (2011) 154-159, Jun. 2011.
Kazutoshi Yamana et al., "Human type 3 5a-reductase is expressed in peripheral tissues at higher levels than types 1 and 2 and its activity is potently inhibited by finasteride and dutasteride", Hormone molecular biology and clinical investigation 2010;2(3):293-299, Aug. 2010.

* cited by examiner

[FIG. 1]
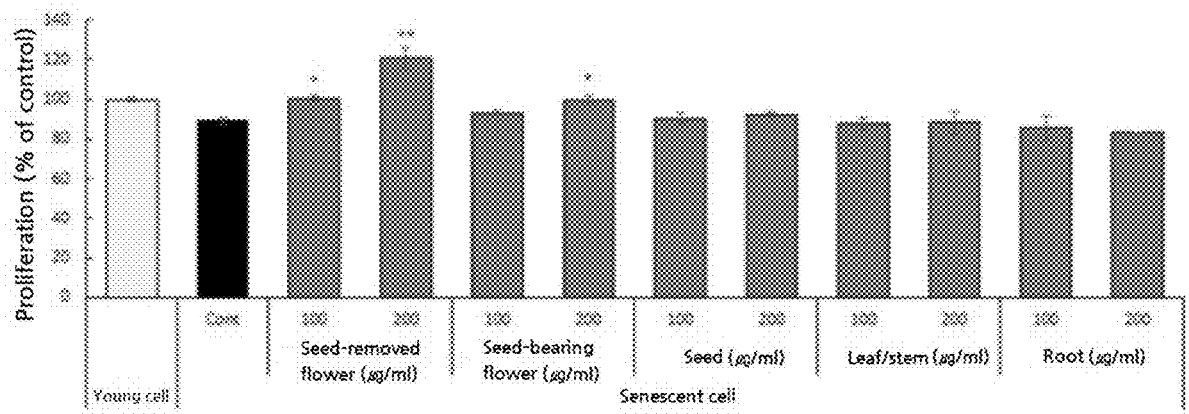
[FIG. 2]
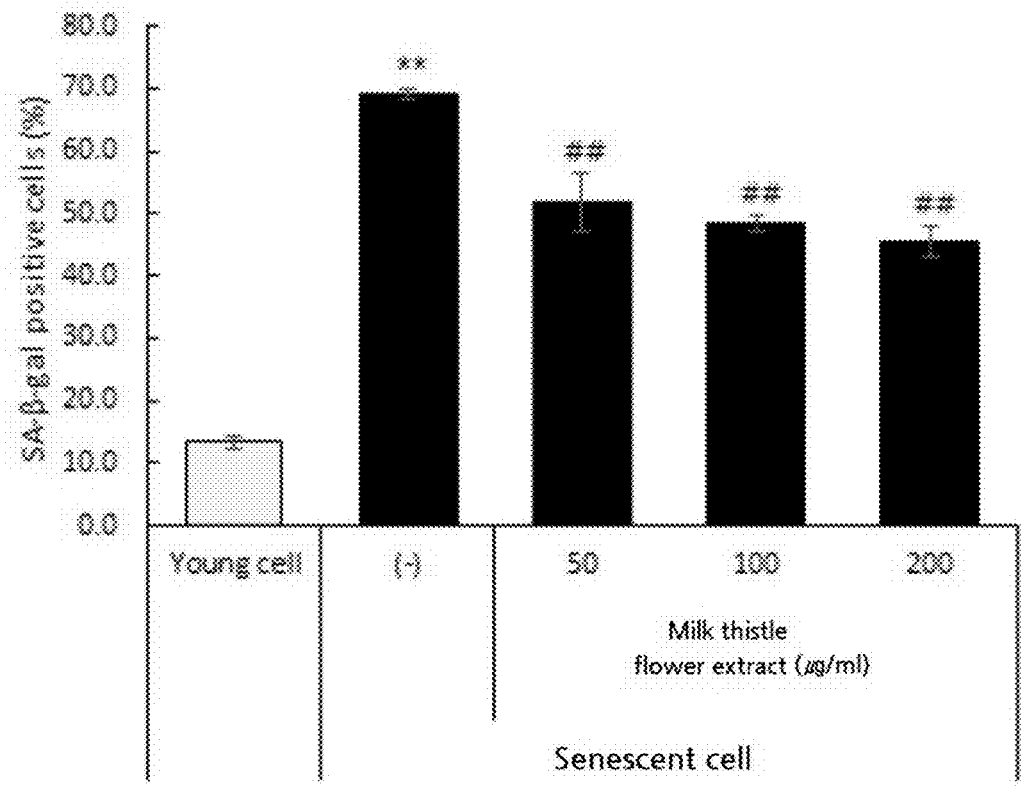

[FIG.3]
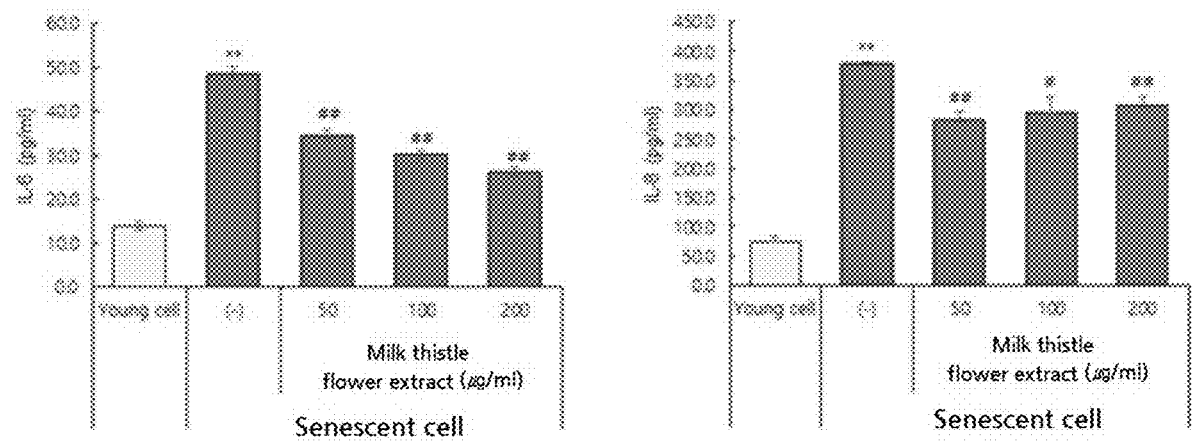

COMPOSITION FOR TREATING HAIR LOSS OR PROMOTING HAIR GROWTH COMPRISING MILK THISTLE FLOWER EXTRACT AS AN ACTIVE INGREDIENT

TECHNICAL FIELD

The present invention relates to a composition for preventing hair loss or promoting hair growth containing a milk thistle flower extract as an active ingredient. More specifically, the present invention relates to a cosmetic composition, pharmaceutical composition and food composition containing a milk thistle flower extract as an active ingredient, which are able to promote hair growth by inducing dermal papilla cell proliferation reduced due to senescence, and activate dermal papilla cells by inhibiting the senescence of dermal papilla cells through inhibition of the activity of senescence-associated β-galactosidase (SA-β-Gal) and the production of senescence-associated secretory phenotypes, thereby preventing hair loss or promoting hair.

BACKGROUND ART

With the development of science, causes of chronic diseases and various treatment methods therefor have been reported in many medical fields. In particular, in modern society, ways to treat psychological problems have also been actively studied. Although hair loss is not a pathological problem, it causes physical and psychological stress. As a result, hair loss can cause secondary diseases such as low self-esteem or social phobia.

Hair loss, which was previously thought to be a part of aging, has become one of the causes that have the greatest influence on appearance since it appears at a high rate even in young people in modern society. People in their 20s and 30s accounted for about 50% of the hair loss population accounted for about 50% of the hair loss population, and the mean ages were 29.8 years for males and 33.6 years for females. 224,688 people were treated for hair loss in 2018. Accordingly, the hair loss treatment market size in South Korea is approaching 4 trillion won, including treatments, medical devices, shampoos, herbal medicines, and the like. It is known that hair loss is caused by various factors, including anemia due to unbalanced eating habits and iron deficiency, side effects of medication, use of strong chemical products such as hair dye or perm, hormonal changes, hypothyroidism, stress, hair handling habits, depression, extreme temperature change, and the like.

Hair loss is broadly divided into two types: scarring alopecia, in which hair follicles are destroyed due to scarring, and thus hair is not regenerated; and non-scarring alopecia, in which hair follicles are maintained without forming scars, and hair is regenerated after symptomatic areas disappear. The application of agents for hair loss treatment or prevention agents is focusing on scarring alopecia. Products that prevents hair loss while promoting hair growth are called anti-hair loss agents, and include hair growth solutions that nourish the root of the hair to grow hair, hair growth promoters that promote blood circulation in the scalp to help prevent hair loss, and hair tonics that turn vellus hair into terminal hair (JY Lim et al., *Kor. J. Aesthet. Cosmetol.*, 12(6):773-786, 2014).

Among scarring alopecia, androgenetic alopecia, in which androgenic hormones are an important etiology, accounts for about 80% of hair loss symptoms. Androgenetic alopecia is known to be caused mainly by genetic factors, the concentration of the male hormone androgen in the blood, and a high concentration of 5-alpha dihydrotestosterone (DHT) which binds to androgen receptors present in scalp hair follicles. DHT regulates hair growth by binding to androgen receptors in the scalp dermal papilla. The binding of DHT to androgen receptors transduces a cell destruction signal to genes of keratinocytes to produce the apoptosis factors DKK-1 and TGF-β1, and finally hair loss occurs due to the destruction of the keratinocytes (Inui S et al., *J Dermatol Sci.*, 61(1):1-6, 2011).

Well-known anti-hair loss agents include minoxidil, which is a skin external preparation approved by the FDA, finasteride for oral use, and dutasteride approved by the Korean MFDS. It is strongly speculated that minoxidil will follow the mechanism of supplying nutrients to hair follicles by dilating blood vessels through hyperpolarization of the cell membrane, but a study was also reported that minoxidil can act directly on human hair follicle cells to activate the signal of beta-catenin, which is a representative proliferation mechanism (Kwack M H et al., *J Dermatol Sci.*, 62(3):154-159, 2011). It is known that finasteride and dutasteride suppress the production of DHT, which causes hair loss, by inhibiting 5α-reductase that converts testosterone into DHT (Yamana K et al., Horm *Mol Biol* Clin Investig., 1; 2(3): 293-299, 2010; Clark R V et al., *J Clin Endocrinol Metab.*, 89(5):2179-2184, 2004). However, chemical anti-hair loss agents, known as hair loss treatments, are ineffective when administration thereof is stopped, and thus continuous administration thereof is required. However, these chemical anti-hair loss agents have various side effects such as dermatitis, decreased libido, and induction of gynecomastia, and thus continuous studies have been conducted to find natural anti-hair loss agents.

The main mechanisms of anti-hair loss agents include a method of activating the proliferation of human dermal papilla cells and related signaling mechanisms, and a method of lowering the production rate of DHT by inhibition of the aforementioned 5-alpha reductase. Dermal papilla cells are cells that are important in the development and growth of hair follicles and have multipotency. The cycle of hair growth is broadly divided into anagen, catagen, telogen, and new anagen stages, and in the anagen stage, dermal papilla cells proliferate, resulting in overall hair growth (Driskell R R et al., *J Cell Sci.*, 15; 124(Pt8):1179-1182, 2011). Several factors are involved in the proliferation of dermal papilla cells, and include FGF-7 that increases the anagen phase, ERK activity that induces cell growth, beta-catenin mechanism that leads to hair follicle development, and Akt activity that inhibits apoptosis (Gentile P et al., Cells., 16; 8(5), doi: 10.3390/cells8050466, 2019).

Milk thistle is a plant belonging to the genus *Silybum* of the family Asteraceae. It is an annual or biennial plant and is characterized by leaves having distinctive white stripes. The genus name "*Silybum*" was derived by *Dioscorides*, an herbalist in ancient Greece who used the term silybon to describe thistle-like plants, and is widely known as milk thistle because milky sap comes out when the leaves are broken. The liver cell protection effect of milk thistle is most well-known, and Korean Patent Application Publication No. 10-2016-0140417 discloses that the use of milk thistle extract together with fermented tea extract and chitooligosaccharide exhibits liver function improvement effects. Milk thistle extract is known to be effective not only in improving liver function but also in reducing total cholesterol levels and treating diabetes, and is also used to prevent motion sickness and heart disease. Since improving liver health, which is the main function of milk thistle, is an effect exhibited by components extracted from milk thistle seeds, parts other than the seeds have been discarded as crop by-products. If these other parts are studied for their physiological activities and may be used as physiologically active ingredients, it is expected that they can provide high added value through recycling of waste resources.

As the hair loss population increases and the age of hair loss patients decreases not only in Korea but also abroad such as China, the United States, and Europe, hair loss is emerging as a major social problem, and thus there is an urgent need to develop a material capable of alleviating hair loss symptoms.

Accordingly, the present inventors have conducted studies on natural materials having little irritation to the human body and capable of activating dermal papilla cells in order to fundamentally solve problems associated with the inactivation of dermal papilla cells caused by senescence, and have conducted studies to find a natural anti-hair loss agent that is able to promote dermal papilla cell proliferation reduced due to senescence and to activate dermal papilla cells by inhibiting the activity of senescence-associated β-galactosidase (SA-β-Gal) and the generation of senescence-associated secretory phenotypes. As a result, the present inventors have found that, among extracts from different parts of milk thistle, an extract from milk thistle flowers from which seeds have been removed has an excellent anti-hair loss effect, thereby completing the present invention.

DISCLOSURE

Technical Problem

An object of the present invention is to provide a cosmetic composition for preventing hair loss or promoting hair growth containing a milk thistle flower extract as an active ingredient.

Another object of the present invention is to provide a pharmaceutical composition for preventing hair loss or promoting hair growth containing a milk thistle flower extract as an active ingredient.

Still another object of the present invention is to provide a food composition for preventing hair loss or promoting hair growth containing a milk thistle flower extract as an active ingredient.

Yet another object of the present invention is to provide a method for preventing hair loss or promoting hair growth, the method comprising a step of administering a composition containing a milk thistle flower extract as an active ingredient.

Technical Solution

To achieve the above objects, the present invention provides a cosmetic composition for preventing hair loss or promoting hair growth containing a milk thistle flower extract as an active ingredient.

The present invention also provides a pharmaceutical composition for preventing hair loss or promoting hair growth containing a milk thistle flower extract as an active ingredient.

The present invention also provides a food composition for preventing hair loss or promoting hair growth containing a milk thistle flower extract as an active ingredient.

The present invention also provides a method for preventing hair loss or promoting hair growth, the method comprising a step of administering a composition containing a milk thistle flower extract as an active ingredient.

Advantageous Effects

The composition for preventing hair loss or promoting hair growth containing a milk thistle flower extract as an active ingredient according to the present invention has no skin irritation and cytotoxicity, and thus has excellent safety for the human safety, and at the same time, is very effective in promoting dermal papilla cell proliferation reduced due to senescence and in activating dermal papilla cells by inhibiting the senescence of dermal papilla cells through inhibition of the activity of senescence-associated β-galactosidase and the generation of senescence-associated secretory phenotypes. Thus, it may be useful as an active ingredient in a cosmetic composition, a pharmaceutical composition or a food composition for preventing hair loss or promoting hair growth.

BRIEF DESCRIPTION OF DRAWINGS

FIG. 1 is a graph showing the results of analyzing the effects of extracts from different parts of milk thistle according to the present invention on the proliferation of dermal papilla cells.

FIG. 2 is a graph showing the effect of an extract of seed-removed milk thistle flowers according to the present invention on the inhibition of senescence-associated β-galactosidase activity.

FIG. 3 is a graph showing the inhibitory effect of the extract of seed-removed milk thistle flowers according to the present invention against the production of senescence-associated secretory phenotypes.

BEST MODE

The present invention relates to a composition for preventing hair loss or promoting hair growth containing a milk thistle flower extract as an active ingredient and the use thereof. More specifically, the present invention relates to a cosmetic composition, pharmaceutical composition, and food composition containing a milk thistle flower extract as an active ingredient. The composition has no skin irritation and cytotoxicity, and thus has excellent safety for the human body, and at the same time, is able to promote dermal papilla cell proliferation reduced due to senescence and to activate dermal papilla cells by inhibiting the senescence of dermal papilla cells through inhibition of the activity of senescence-related β-galactosidase and the production of senescence-related secretory phenotypes (IL-6 and IL-8), thereby effectively preventing hair loss or promoting hair growth.

In one aspect, the present invention provides a composition for preventing hair loss or promoting hair growth containing a milk thistle flower extract as an active ingredient.

As used herein, the term "milk thistle" refers to plants belonging to the genus *Silybum* of the family Asteraceae, and includes *Silybum marianum* and *Silybum eburneum*. *Silybum marianum* means sacred milk thistle and is found throughout Europe, Asia, North Africa, China, Australia, etc. *Silybum eburneum* is called silver milk thistle or elephant thistle, and is mainly native to Algeria, Morocco, and Spain. All parts of milk thistle are edible, and the leaves, stems, roots and seeds thereof are mainly used.

As used herein, the term "milk thistle flower" refers to a flower containing or not containing a milk thistle seed, and preferably refers to a part remaining after removal of the seed from the flower of milk thistle.

As used herein, the term "extract" refers to a product, such as a liquid ingredient obtained by immersing a material of interest in various solvents, followed by extraction and fractionation at room temperature or elevated temperature for a certain period of time, or a solid obtained by removing the solvent from the liquid component. The term "extract" may be construed comprehensively to include, in addition to the product, a dilution of the product, a concentrate thereof, a crude product thereof, a purification product thereof, and the like.

The milk thistle flower extract may be obtained by extraction with water or various organic solvents. Here, the organic solvent that is used for extraction is not particularly limited as long as it is possible to obtain an extract having an effect of preventing hair loss or promoting hair growth. However, the solvent may preferably be water, a polar solvent, or a non-polar solvent. More preferably, the solvent may be water, a $C_1$-$C_4$ lower alcohol (ethanol, methanol, propanol, butanol, etc.), a mixed solvent thereof, or the like, preferably ethanol.

In addition, a method for obtaining the extract is not particularly limited as long as it is possible to obtain an extract having an effect of preventing hair loss or promoting hair growth. Examples of the extraction method include maceration, ultrasonic extraction, or reflux cooling extraction, preferably ultrasonic extraction.

The ultrasonic extraction is a method of extracting useful components from various natural materials at room temperature by physical force rather than chemical force by using a vibration element having a frequency of at least 20,000 per second, and has advantages over solvent extraction, vegetable oil extraction or steam distillation extraction in that it is able to extract a high concentration of an active ingredient from a natural material without destroying the active ingredient.

In one specific embodiment, the ultrasonic extraction may be performed on dried milk thistle flower powder using a 60% to 80% ethanol solution at room temperature for 24 to 72 hours. Preferably, it is performed using a 65% to 75% ethanol solution at room temperature for 36 hours to 60 hours. More preferably, the ultrasonic extraction is performed using a 70% ethanol solution at room temperature for 48 hours. If each condition is lower than the lower limit of the above range, the active ingredient of the present invention will not be sufficiently extracted from milk thistle flowers, and if each condition is higher than the upper limit of the above range, the amount of the active ingredient extracted will not significantly increase, impurities other than the active ingredient will be extracted, and the efficiency of the process will decrease.

The obtained milk thistle flower extract may be concentrated under reduced pressure using, but not limited to, a vacuum concentrator or a vacuum rotary evaporator. In addition, after concentration under reduced pressure, the concentrate may be dried through, but not limited to, lyophilization, vacuum drying, vacuum drying, boiling drying, or spray drying.

As used herein, "hair loss" refers to a state in which there is no hair in an area where hair should be normally present. Specifically, it means that the terminal hair (thick and black hair) of the scalp is lost. The cause of hair loss is not limited, but examples thereof include hereditary androgenetic alopecia (baldness), alopecia areata, ringworm of the head due to fungal infection, telogen effluvium, trichotillomania, hair production disorders, etc. Examples of scarring alopecia include hair loss caused by lupus, folliculitis decalvans, lichen planus pilaris, and hair loss caused by burns and trauma.

As used herein, the term "prevention" or "preventing" means preventing a certain event or phenomenon from occurring, and "preventing hair loss" means preventing hair loss from occurring.

As used herein, "hair growth" means that hair grows in the hair follicle. The "hair" is meant to include the hair roots and hair follicles of the head, hair, eyelashes, eyebrows, beard, hircus, pubic hair, and all parts of the body with hair roots and hair follicles.

As used herein, "promotion" or "promoting" means an increase of 0.5% or more, preferably 1% or more, compared to before the occurrence of a certain event or phenomenon, and "promoting hair growth" means that hair growth increases by 0.5% or more compared to before the occurrence of the phenomenon.

In the present invention, the effect of preventing hair loss or promoting hair growth is achieved by promoting dermal papilla cell proliferation reduced due to senescence and activating dermal papilla cells by inhibiting the senescence of dermal papilla cells through inhibition of the activity of senescence-related β-galactosidase (SA-β-Gal) and the generation of senescence-related secretory phenotypes. The above effect may be achieved by the milk thistle flower extract, in particular, an extract of a flower part remaining after removing the seed from the milk thistle flower.

In one example of the present invention, in order to evaluate the effect of the milk thistle extract on the prevention of hair loss or the promotion of hair growth, analysis was performed on the effects of the milk thistle extract on the proliferation of dermal papilla cells, the inhibition of senescence-associated β-galactosidase, and the inhibition of production of senescence-associated secretory phenotypes. As a result, it could be confirmed that the milk thistle extract, that is, an extract from a flower remaining after removing the seed from the milk thistle flower, significantly inhibited the proliferation of dermal papilla cells, inhibited the activity of senescence-associated β-galactosidase in a concentration-dependent manner, and effectively inhibited the production of senescence-associated secretory phenotypes, compared to other milk thistle extracts (see FIGS. 1 to 3).

As described above, the milk thistle flower extract provided in the present invention exhibits the effect of promoting hair growth by inducing dermal papilla cell proliferation reduced due to senescence, and has the effect of inhibiting the senescence of dermal papilla cells, which is one of the causes of hair loss. In addition, the milk thistle flower extract provided in the present invention is able to prevent hair loss by inhibiting the activity of senescence-related β-galactosidase and inhibiting the production of senescence-related secretion phenotypes (IL-6 and IL-8). Accordingly, the milk thistle flower extract of the present invention may be effectively used as an active ingredient in a cosmetic composition, pharmaceutical composition or food composition for preventing hair loss and promoting hair growth.

The content of the milk thistle flower extract in the composition is not particularly limited, but may be 0.00001 to 100 wt %, preferably 0.0001 to 30 wt %, more preferably 0.001 to 20 wt %, even more preferably 0.001 to 10 wt %, based on the total weight of the composition. If the content of the milk thistle flower extract in the composition is less than 0.0001 wt %, the efficacy thereof will be insignificant. In addition, if the content is more than 15 wt %, the increase in the effect by the increase in the content will be insignificant, and a problem may arise in that the stability of the formulation of cosmetics, pharmaceuticals, and foods is not ensured.

In one specific embodiment, the composition for preventing hair loss or promoting hair growth containing the milk thistle flower extract according to the present invention may be provided as a cosmetic composition for preventing hair loss or promoting hair growth.

In the present invention, the "cosmetic composition" may be a cosmetic composition selected from among hair tonic, hair cream, hair lotion, hair shampoo, hair rinse, hair conditioner, hair spray, hair aerosol, pomade, powder, gel, sol-gel, emulsion, oil, wax, and aerosol.

The cosmetic composition may contain conventional adjuvants or cosmetically acceptable carriers, such as stabilizers, solubilizers, vitamins, pigments, and fragrances, which are commonly used in the field of cosmetic compositions.

The cosmetic composition may contain a moisturizer, an anti-inflammatory agent, an antibacterial agent, an antifungal agent, vitamins, a sunscreen agent, an antibiotic, a perfume, and a dye, if necessary.

Specifically, the cosmetic composition may be prepared in any formulation, which is conventionally prepared in the art. For example, it may be formulated into a solution, emulsion, suspension, paste, cream, lotion, gel, powder, spray, surfactant-containing cleansing, oil, soap, liquid cleanser, bath additive, foundation, makeup base, essence, toner, foam, pack, softening lotion, sunscreen cream, or sun oil, etc., without being limited thereto.

When the formulation of the present invention is a solution or emulsion, it may contain, as carrier components, a solvent, a solubilizing agent or an emulsifying agent, for example, water, ethanol, isopropanol, ethyl carbonate, ethyl acetate, benzyl alcohol, benzyl benzoate, propylene glycol, 1,3-butyl glycol oil, glycerol fatty ester, polyethylene glycol, or sorbitan fatty acid ester.

When the formulation of the present invention is a suspension, it may contain, as carrier components, a liquid diluent, such as water, ethanol or propylene glycol, and a suspending agent, such as ethoxylated isostearyl alcohol, polyoxyethylene sorbitol ester, or polyoxyethylene sorbitan ester, microcrystalline cellulose, aluminum metahydroxide, bentonite, or tragacanth.

When the formulation of the present invention is a paste, cream or gel, it may contain, as carrier components, animal oil, vegetable oil, wax, paraffin, starch, tragacanth, cellulose derivatives, polyethylene glycol, silicone, bentonite, silica, talc, or zinc oxide.

When the formulation of the present invention is powder or spray, it may contain, as carrier components, lactose, talc, silica, aluminum hydroxide, calcium silicate, or polyamide powder. Particularly, when it is spray, it may additionally contain a propellant, such as chlorofluorohydrocarbon, propane/butane, or dimethyl ether.

When the formulation of the present invention is a surfactant-containing cleansing oil, it may contain, as carrier components, aliphatic alcohol sulfate, aliphatic alcohol ether sulfate, sulfosuccinic monoester, isethionate, imidazolium derivatives, methyl taurate, sarcosinate, fatty acid amide ether sulfate, alkyl amido betaine, aliphatic alcohol, fatty acid glyceride, fatty acid diethanolamide, vegetable oil, lanoline derivatives, or ethoxylated glycerol fatty acid ester.

The carrier may be a non-naturally occurring carrier.

In another specific embodiment, the composition for preventing hair loss or promoting hair growth containing the milk thistle flower extract according to the present invention may be provided as a pharmaceutical composition for preventing hair loss or promoting hair growth.

As used herein, the term "pharmaceutical composition" means one prepared for the purpose of preventing or treating a disease. For use, the pharmaceutical composition may be formulated in various forms according to conventional methods. For example, it may be formulated in oral dosage forms such as powders, granules, tablets, capsules, suspensions, emulsions, syrups, aerosols, etc., or may be formulated in parenteral dosage forms using diluents or excipients such as lubricants, wetting agents, flavoring agents, emulsifiers, suspending agents, preservatives, surfactants, etc. In addition, it may be formulated and used in dosage forms such as external preparations, suppositories, skin external preparations, and sterile injectable solutions. Specifically, the composition of the present invention may be used by a method such as directly applying or spreading the composition to the hair or scalp. Hair to which the composition of the present invention includes the hair roots and hair follicles of the head, hair, eyelashes, eyebrows, beard, hircus, pubic hair, and all parts of the body with hair roots and hair follicles.

In addition, the pharmaceutical composition may be prepared to further contain carriers known in the art, such as pharmaceutically acceptable carriers such as buffers, pain relievers, solubilizers, isotonic agents, stabilizers, and bases, according to each formulation. As used herein, the term "pharmaceutically acceptable carrier" may refer to a carrier or diluent that neither causes irritation to an organism nor abolishes biological activities or properties of an active ingredient to be administered thereto. Types of carriers that may be used in the present invention are not particularly limited, and any carrier may be used as long as it is conventionally used in the art and is pharmaceutically acceptable. Non-limiting examples of the carrier include saline, sterile water, Ringer's solution, buffered saline, an albumin injection solution, a dextrose solution, a maltodextrin solution, glycerol, ethanol, etc. These carriers may be used alone or in combination of two or more. The carrier may be a non-naturally occurring carrier.

The invention of the present invention may be administered in a pharmaceutically effective amount. The term "pharmaceutically effective amount" refers to an amount that is sufficient to treat a disease at a reasonable benefit/risk ratio applicable to any medical treatment and causes no side effects. The effective dose level may be determined depending on factors, the patient's health status, the type and severity of disease, the activity of the drug, sensitivity to the drug, the mode of administration, the time of administration, excretion rate, the duration of treatment, the drug content, and drugs used in combination with the composition, as well as other factors well known in the medical field. Specifically, the effective dose is generally 0.01 mg to 5000 mg per day per 1 kg of the body weight of the subject to be administered, and the pharmaceutical composition may be administered once or several times a day at regular time intervals according to the judgment of a doctor or pharmacist, without being limited thereto.

In addition, the pharmaceutical composition of the present invention may be used alone or in combination with other pharmaceutically active compounds exhibiting an effect of preventing or improving hair loss-related diseases or in a suitable set.

The pharmaceutical composition of the present invention may be administered as an individual therapeutic agent or in combination with other therapeutic agents, and may be administered sequentially or simultaneously with conventional therapeutic agents. The pharmaceutical composition may be administered in a single or multiple dosage form. It is important to administer the pharmaceutical composition in the minimum amount that can exhibit the maximum effect without causing side effects, in view of all the above-described factors, and this amount can be easily determined by a person skilled in the art.

For example, in addition to the pharmaceutical composition containing the milk thistle flower extract as an active ingredient according to the present invention, a conventional hair loss treatment selected from among minoxidil, finasteride and spironolactone may be selected and additionally administered.

As used herein, the term "administration" or "administering" means introducing the pharmaceutical composition of the present invention to a subject by any suitable method. The composition of the present invention may be administered orally or parenterally through various routes as long as it can reach the target tissue.

The mode of administration of the pharmaceutical composition according to the present invention is not particularly limited, and may follow a method commonly used in the art. As a non-limiting example of the mode of administration, the composition may be administered by orally or parenterally. Specifically, the composition of the present invention may be used by a method such as directly applying or spreading the composition to the hair or scalp.

The pharmaceutical composition according to the present invention may be prepared into various formulations depending on the desired mode of administration.

The frequency of administration of the composition of the present invention is not particularly limited, but the composition may be administered once a day or may be administered several times a day at divided doses.

In another specific embodiment, the composition for preventing hair loss or promoting hair growth containing the milk thistle flower extract according to the present invention may be provided as a food composition for preventing hair loss or promoting hair growth.

When the composition of the present invention is used as a food additive, the milk thistle flower extract may be added alone or used together with other foods or food ingredients, and may be appropriately used according to a conventional method. The content of the active ingredient in the composition may be appropriately determined according to the purpose of use (prevention, health, or therapeutic treatment), and the composition may further contain food additives acceptable in food science. Since the composition of the present invention contains, as an active ingredient, an extract derived from a natural product, there is no problem in terms of stability, and there is no great limitation on the content of the active ingredient.

The term "food composition" in the present invention may include all conventional foods, and may be used interchangeably with terms known in the art, such as functional food and health functional food.

As used herein, the term "health functional food" refers to a food manufactured and processed using raw materials or ingredients that have functionality beneficial for the human body, and the term "functionality" means that the intake of food is directed to controlling nutriments on the structure and function of the human body or achieving useful effects on health such as physiological effects.

In addition, the term "health functional food" as used herein refers to a food containing a specific ingredient or manufactured and processed by extracting, concentrating, refining, mixing, etc. of a specific ingredient contained in a food raw material for the purpose of health supplementation, and refers to a food designed and processed to sufficiently exert bio-regulatory functions such as biodefense, regulation of biorhythm, prevention and recovery of disease, etc., by the above ingredient. The health food composition may perform functions related to disease prevention and recovery from diseases.

There is no limitation on the type of food to which the composition for preventing hair loss or promoting hair growth according to the present invention may be added. In addition, the composition containing the milk thistle flower extract as active ingredient according to the present invention may be prepared by mixing the extract with appropriate auxiliary ingredients and known additives that may be contained in foods depending on the choice of those skilled in the art. Examples of food to which the composition of the present invention may be added include meats, sausages, bread, chocolate, candies, snack, confectionery, pizza, noodles, gum, dairy products including ice cream, various soups, beverages, teas, drinks, alcoholic beverages, and multi-vitamin preparations. These foods may be prepared by adding the extract and a fraction thereof as an active ingredient according to the present invention to juices, teas, jellies, etc.

In addition, foods that may be applied to the present invention include, for example, all foods such as special nutritional foods (e.g., formula milk, infant and baby food, etc.), processed meat products, fish meat products, tofu, jelly, noodles (e.g., ramen, noodles, etc.), health supplements, seasonings (e.g. soy sauce, soybean paste, gochujang, mixed paste, etc.), sauces, confectionery (e.g. snacks), dairy products (e.g. fermented milk, cheese, etc.), other processed foods, kimchi, pickled foods (various types of kimchi, pickled vegetables, etc.), beverages (e.g., fruit drinks, vegetable drinks, soy milk, fermented beverages, etc.), natural seasonings (e.g., ramen soup, etc.).

When the health functional food composition of the present invention is used as a beverage, it may further contain various sweeteners, flavoring agents, or natural carbohydrates, like conventional beverages. In addition, the health functional food composition of the present invention may contain various nutrients, vitamins, minerals, flavoring agents, colorants, pectic acid and its salt, alginic acid and its salt, organic acids, protective colloidal thickeners, pH adjusting agents, stabilizers, preservatives, glycerin, alcohol, carbonizing agents that are used in carbonated beverages, etc. Additionally, the health functional food composition of the present invention may contain fruit flesh that is used for the preparation of natural fruit juice, fruit juice beverages or vegetable beverages.

The milk thistle flower extract of the present invention, more specifically, the milk thistle flower ethanol extract, is obtained from the natural medicinal plant as a raw material, and thus even when it is used as a cosmetic composition, pharmaceutical composition, or food composition, side effects thereof are less than those of general synthetic compounds. Accordingly, it may be contained safely and used usefully.

In another aspect, the present invention provides a method for preventing or treating a hair loss-related disease, the method comprising a step of administering the composition containing the milk thistle flower extract.

As used herein, the term "subject" may refer to any animals, including humans, who have or may have a hair loss-related disease. The animals include, but are not limited to, not only humans but also mammals such as cattle, horses, sheep, pigs, goats, camels, antelopes, dogs, and cats, in need of treatment for a similar symptom to the humans.

The method for preventing or treating a hair loss-related disease according to the present invention may comprise a step of a pharmaceutically effective amount of the composition to a subject having or being at risk of having a hair loss-related disease. The method for administration is as described above.

The term "prevention" or "preventing" may mean any action that suppresses or delays the onset of a hair loss-related disease by administering the composition for preventing hair loss or promoting hair growth according to the present invention to a subject.

The term "treatment" or "treating" may refer to any action that alleviates or beneficially changes the symptoms of a hair loss-related disease by administering the composition of the present invention to a subject suspected of having the hair loss-related disease.

The composition containing the milk thistle flower extract is as described above.

For administration, the composition of the present invention may contain a pharmaceutically acceptable carrier, excipient or diluent in addition to the active ingredients described above. Examples of the carrier, excipient and diluent include lactose, dextrose, sucrose, sorbitol, mannitol, starch, acacia gum, alginate, gelatin, calcium silicate, microcrystalline cellulose, polyvinylpyrrolidone, cellulose, water, syrup, methyl cellulose, methylhydroxybenzoate, propylhydroxybenzoate, talc, magnesium stearate, and mineral oil.

A suitable dosage of the composition of the present invention varies depending on the condition and weight of a patient, the severity of the disease, the type of drug, and the time of administration, but may be appropriately selected by those skilled in the art. Specifically, the dose of the milk thistle flower extract may be 50 to 500 mg/kg.

Examples of the hair loss-related disease include, but are not limited to, alopecia areata, androgenetic alopecia, telogen effluvium, trichotillomania, anagen effluvium such as pressure alopecia, pityroid alopecia, alopecia syphlltiac, alopecia seborrhecia, symptomatic alopecia, scarring alopecia, and congenital alopecia, as well as any disease caused by hair loss from the hair follicle.

MODE FOR INVENTION

Hereinafter, the present invention will be described in detail by way of examples to assist in the understanding of the present invention. However, the examples according to the present invention may be modified in many different forms, and the scope of the present invention should not be construed as being limited to the following examples. Examples of the present invention are provided to explain the present invention in more detail to those skilled in the art.

Example 1: Preparation of Extracts from Different Parts of Milk Thistle

The flower, above-ground leaf and stem, and root parts of milk thistle (*Silybum marianum*) were collected separately. In the case of flowers, flowers from which seeds have been removed and flowers from which seeds have not been removed were prepared separately. Each of the collected parts was washed thoroughly to completely remove foreign substances and impurities, dried in the shade at 20° C. to 35° C., and then ground to a particle size of 1 mm or less. Thereafter, 100 g of each powder for each part of milk thistle was immersed in a 70% ethanol solvent and extracted ultrasonically for 48 hours, and then each of the obtained extracts was filtered through filter paper (Advantec, No. 2). The filtrates were concentrated under reduced pressure, thereby preparing extracts of different parts of milk thistle.

Example 2: Production of Replicative Senescent Cells

In order to induce replicative senescence, human hair follicle dermal papilla cells (HFDPCs) were purchased from PromoCell (Heidelberg, Germany). Human dermal papilla cells were grown in a dermal papilla cell growth medium containing supplementMix, and then seeded in a 100 mm culture dish at a density of $4 \times 10^5$ cells and cultured in an incubator at 37° C. under 5% $CO_2$. When the cells reached a confluence of about 80 to 90% in the culture dish, the cells were detached by treatment with trypsin-EDTA and counted, and the degree of growth of the cells was examined by measuring the cell population doubling time (DT) according to Equation 1 below. Replicative senescence was induced while continuously subculturing the cells in the same manner as above. The DT of young dermal papilla cells was 1.5 days and the DT of replicative senescent dermal papilla cells was 10.9 days. The degree of cellular senescence was examined by staining of senescence-associated beta-galactosidase or ELISA of senescence-associated secretory phenotypes (SASPs) (IL-6 and IL-8).

$$DT=(T-T_0)/3.32\times(\log N-\log N_0) \quad \text{[Equation 1]}$$

($N$=number of cells grown in culture dish, $N_0$=number of cells seeded, $T-T_0$=days of cell culture)

Example 3: In Vitro Measurement of Effects of Extracts of Different Parts of Milk Thistle on Proliferation of Dermal Papilla Cells In order to examine the effects of the extracts of different parts of milk thistle on the proliferation of dermal papilla cells, which are the main cells for hair growth, the proliferation of dermal papilla cells was measured. Specifically, human hair follicle dermal papilla cells (HFDPCs, Promo-Cell) were grown in a dermal papilla cell growth medium containing supplementMix, and then seeded in a 24-well plate at a density of $1.5 \times 10^4$ cells/well and cultured in an incubator at 37° C. in 5% $CO_2$ for 24 hours. After dissolving the extract of each part of milk thistle in culture medium, each well was treated with the culture medium and incubated for 72 hours. After 72 hours, the cell culture supernatant was removed, MTT reagent (1 mg/ml) was diluted 10-fold and mixed with culture medium, and then each well was treated with the MTT reagent solution and incubated for 2 hours. After 2 hours, the MTT reagent was removed, 200 μl of DMSO was added to each well to dissolve formazan, and the absorbance at 540 nm was measured. The results of the measurement are shown in FIG. 1.

As shown in FIG. 1, it was confirmed that the proliferation of replicative senescent dermal papilla cells reduced compared to young cells increased in a concentration-dependent manner compared to the control group when the senescent dermal papilla cells were treated with the extract of seed-removed milk thistle flowers, whereas the extracts of the other parts on the promotion of cell proliferation were not significant. In addition, it was confirmed that cell proliferation was more promoted by the seed-removed flower extract than by the seed-bearing flower extract.

Example 4: In Vitro Measurement of Inhibitory Effect of Extract of Seed-Removed Milk Thistle Flowers Against Senescence-Associated s-Galactosidase Activity Dermal papilla cells were seeded in a 6-well plate ($2\times10^5$ cells/well) and cultured in an incubator for 24 hours at 37° C. under a 5% $CO_2$. Based on the results of Example 3, the seed-removed milk thistle flower extract confirmed to increase the proliferation of replicative senescent dermal papilla cells reduced compared to that of young cells was dissolved in culture medium, and then each well containing the cultured cells was treated with the extract solution and incubated for 72 hours. After 72 hours, the cell culture supernatant was removed, and the cells were detached by treatment with trypsin-EDTA, stained fluorescently with SPiDER-βGal (Dojindo, Japan) for 15 minutes, and counted by flow cytometry (FACS Calibur, Becton Dickinson, San Jose, CA). Changes in cellular senescence were observed by checking the proportion of cells showing senescence-associated β-galactosidase activity.

The resulting values were expressed as values relative to 100% for the control group, and the results are shown in FIG. 2.

As shown in FIG. 2, it was confirmed that the seed-removed milk thistle flower extract exhibited an excellent ability to inhibit senescence-associated β-galactosidase activity in the replicative senescent cells in a concentration-dependent manner.

Example 5: In Vitro Measurement of Inhibitory Effect of Seed-Removed Milk Thistle Flower Extract Against Production of Senescence-Associated Secretory Phenotypes Dermal papilla cells were seeded in a 6-well plate ($2\times10^5$ cells/well) and cultured in an incubator for 24 hours at 37° C. under a 5% $CO_2$. The extract of seed-removed milk thistle flowers was dissolved in culture medium, and the each well containing the cultured cells was treated with the extract solution and incubated for 72 hours. After 72 hours, the cell culture supernatant was collected, and the concentrations of the senescence-associated secretory phenotypes IL-6 and IL-8 in the cell culture were measured using the Human IL-6 Quantikine ELISA Kit or IL-8/CXCL8 ELISA Kit (R&D systems, USA). The results are shown in FIG. 3.

As shown in FIG. 3, it was confirmed that the extract of seed-removed milk thistle flowers reduced IL-6 and IL-8 in both the young cells and the replicative senescent cells compared to the untreated group. Thereby, it was confirmed that the extract of seed-removed milk thistle flowers activated the dermal papilla cells by inhibiting the production of the senescence-associated secretory cells.

Example 6: Human Skin Safety Test for Seed-Removed Milk Thistle Flower Extract In order to confirm that the extract of seed-removed milk thistle flowers according to the present invention is safe for human skin, a skin safety verification test was performed. To this end, a repeated insult patch test was conducted.

Nourishing creams containing the seed-removed milk thistle extract of Example 1 in amounts of 0.1%, 0.5% and 1%, respectively, were prepared. Specifically, a water phase containing purified water, triethanolamine and propylene glycol was dissolved by heating to 70° C. and then emulsified by adding a solution obtained by dissolving beeswax, liquid paraffin, an oil component, an emulsifier and a preservative by heating to 70° C. After completion of emulsification, the solution was cooled to 45° C., and the seed-removed milk thistle flower extract was added thereto in amounts of 0.1%, 0.5% and 1% and dispersed therein, followed by cooling to 30° C. As the content of the extract of seed-removed milk thistle flowers was increased from 0.1% to 0.5% and 1%, the content of liquid paraffin was decreased from 9.91% to 9.51% and 9.01%, respectively, thereby preparing nourishing creams.

Using the nourishing creams prepared as described above, a repeated insult patch test was conducted on the upper arm areas of 30 healthy adults every other day for a total of 9 times for 24 hours per time to determine whether the extract of seed-removed milk thistle flowers irritated the skin.

The patch test was performed using a Finn chamber (Epitest Ltd., Finland). 15 μl of each of the external skin preparations was dropped into the chamber, and then the patch test was performed. The degree of skin reaction in each patch test was scored using the following Equation 2, and the results are shown in Table 1 below.

$$\text{Average degree of reaction} = [[(\text{reaction index} \times \text{degree of reaction})/(\text{total number of subjects} \times \text{highest score (4)})] \times 100] \div \text{number of tests (9)} \quad \text{[Equation 2]}$$

In the degree of reaction, ± represents a score of 1 point, ± represents a score of 2, and ++ represents a score of 4. When the average degree of reaction is less than 3, the corresponding composition is determined to be safe.

TABLE 1

| | Number of subjects showing reaction | | | | | | | | | |
|---|---|---|---|---|---|---|---|---|---|---|
| | Week 1 | | | Week 2 | | | Week 3 | | | Average |
| Test substance | 1st ± + + + | 2nd ± + + + | 3rd ± + + + | 4th ± + + + | 5th ± + + + | 6th ± + + + | 7th ± + + + | 8th ± + + + | 9th ± + + + | degree of reaction |
| Control (squalene) | 1 - - | | 1 - - | - - - | - - - | - - - | - - - | - - - | - - - | 0.18 |
| Milk thistle flower extract (0.1%) [test group 1] | 0 - - | | 0 - - | - - - | - - - | - - - | - - - | - - - | - - - | 0.00 |
| Milk thistle flower extract (0.5%) [test group 2] | 0 - - | | 0 - - | - - - | - - - | - - - | - - - | - - - | - - - | 0.00 |
| Milk thistle flower extract (1%) [test group 3] | 0 - - | | 0 - - | - - - | - - - | - - - | - - - | - - - | - - - | 0.00 |

As shown in Table 1 above, the number of subjects corresponding to ±, + and ++ was 0 in all of test groups 1, 2 and 3, and the average degree of reaction was also 0.00. As a result of the above test, it was determined that the extract of seed-removed milk thistle flowers according to the present invention showed an average degree of reaction of 3 or less, indicating that it is a safe substance that shows no remarkable cumulative irritation aspect.

The composition of the present invention may be prepared by the following Formulation Examples, without being limited thereto.

Formulation Example 1: Cosmetic Formulations

Formulation Example 1-1: Softening Lotion

As shown in Table 2 below, a softening lotion containing the milk thistle flower extract as an active ingredient was prepared according to a conventional method.

TABLE 2

| Component | wt % |
|---|---|
| Milk thistle flower extract | 0.01 |
| Glycerin | 3.0 |
| Butylene glycol | 2.0 |
| Propylene glycol | 2.0 |
| Carboxyvinyl polymer | 0.1 |
| Ethanol | 10.0 |
| Triethanolamine | 0.1 |
| Preservative, trace colorant, trace fragrance and trace purified water | 82.79 |
| Sum | 100.0 |

Formulation Example 1-2: Nourishing Lotion

As shown in Table 3 below, a nourishing lotion containing the milk thistle flower extract as an active ingredient was prepared according to a conventional method.

TABLE 3

| Component | wt % |
|---|---|
| Milk thistle flower extract | 0.01 |
| Beeswax | 4.0 |
| Polysorbate 60 | 1.5 |
| Sorbitan sesquioleate | 0.5 |
| Liquid paraffin | 5.0 |
| Squalene | 5.0 |
| Caprylic/capric triglyceride | 5.0 |
| Glycerin | 3.0 |
| Butylene glycol | 3.0 |
| Propylene glycol | 3.0 |
| Carboxyvinyl polymer | 0.1 |
| Triethanolamine | 0.2 |
| Preservative, trace colorant, trace fragrance and trace purified water | 69.69 |
| Sum | 100.0 |

Formulation Example 1-3: Nourishing Cream

As shown in Table 4 below, a nourishing lotion containing the milk thistle flower extract as an active ingredient was prepared according to a conventional method.

TABLE 4

| Component | wt % |
|---|---|
| Milk thistle flower extract | 0.01 |
| Beeswax | 10.0 |
| Polysorbate 60 | 1.5 |
| Sorbitan sesquioleate | 0.5 |
| Liquid paraffin | 10.0 |
| Squalene | 5.0 |
| Caprylic/capric triglyceride | 5.0 |
| Glycerin | 5.0 |
| Butylene glycol | 3.0 |
| Propylene glycol | 3.0 |
| Triethanolamine | 0.2 |
| Preservative, trace colorant, trace fragrance and trace purified water | 56.79 |
| Sum | 100.0 |

Formulation Example 1-4: Massage Cream

As shown in Table 5 below, a massage cream containing the milk thistle flower extract as an active ingredient was prepared according to a conventional method.

TABLE 5

| Component | wt % |
|---|---|
| Milk thistle flower extract | 0.01 |
| Beeswax | 10.0 |
| Polysorbate 60 | 1.5 |
| Sorbitan sesquioleate | 0.8 |
| Liquid paraffin | 40.0 |
| Squalene | 5.0 |
| Caprylic/capric triglyceride | 4.0 |
| Glycerin | 5.0 |
| Butylene glycol | 3.0 |
| Propylene glycol | 3.0 |
| Triethanolamine | 0.2 |
| Preservative, trace colorant, trace fragrance and trace purified water | 27.49 |
| Sum | 100.0 |

Formulation Example 1-5: Pack

As shown in Table 6 below, a pack containing the milk thistle flower extract as an active ingredient was prepared according to a conventional method.

TABLE 6

| Component | wt % |
|---|---|
| Milk thistle flower extract | 0.01 |
| Polyvinyl alcohol | 13.0 |
| Sodium carboxymethyl cellulose | 0.2 |
| Allantoin | 0.1 |
| Ethanol | 5.0 |
| Nonylphenyl ether | 0.3 |
| Preservative, trace colorant, trace fragrance and trace purified water | 81.39 |
| Sum | 100.0 |

Formulation Example 2: Pharmaceutical Formulations

Formulation Example 2-1: Preparation of Powder

TABLE 7

| Component | Content (g) |
|---|---|
| Milk thistle flower extract | 2 |
| Lactose | 1 |

Powder was prepared by mixing the above components and filling an airtight bag with the mixture.

Formulation Example 2-2: Preparation of Tablet

TABLE 8

| Component | Content (mg) |
|---|---|
| Milk thistle flower extract | 100 |
| Corn starch | 100 |
| Lactose | 100 |
| Magnesium stearate | 2 |

A tablet was prepared by mixing the above components and tableting the mixture according to a conventional tablet preparation method.

Formulation Example 2-3: Preparation of Capsule

TABLE 9

| Component | Content (mg) |
|---|---|
| Milk thistle flower extract | 100 |
| Corn starch | 100 |
| Lactose | 100 |
| Magnesium stearate | 2 |

A capsule was prepared by mixing the above components and filling a gelatin capsule with the mixture according to a conventional capsule preparation method.

Formulation Example 2-4: Preparation of Gel

TABLE 10

| Component | wt % |
|---|---|
| Milk thistle flower extract | 1.00 |
| Butylene glycol | 2.00 |
| Glycerin | 1.00 |
| Disodium EDTA | 0.02 |
| PEG-60 hydrogenated castor oil | 1.00 |
| Cocamidopropyl betaine | 4.00 |
| Lauryl glucoside | 6.00 |
| Polysorbate 20 | 1.00 |
| Sodium benzoate | 0.40 |
| caprylic glycol | 0.20 |
| Sodium lactate | 0.50 |
| Hydroxyethyl cellulose | 0.7 |
| Purified water | 82.18 |
| Sum | 100.0 |

The above components were mixed together, and then a gel containing the milk thistle flower extract as an active ingredient was prepared using the mixture according to a conventional method.

Formulation Example 2-4: Preparation of Ointment

TABLE 11

| Component | wt % |
|---|---|
| Milk thistle flower extract | 1.0 |
| Diethanolamine | 1.5 |
| Polyvinyl pyrrolidone | 5.0 |
| Propylene glycol | 30.0 |
| Purified water | 62.5 |
| Sum | 100.0 |

The invention claimed is:

1. A method for treating a hair loss-related disease, the method comprising administering a composition comprising a milk thistle flower extract from which seeds have been removed as an active ingredient.

2. The method according to claim 1, wherein the hair loss-related disease is alopecia areata, androgenetic alopecia, telogen effluvium, anagen effluvium, pityroid alopecia, alopecia syphlltiac, alopecia seborrhecia, symptomatic alopecia, scarring alopecia, or congenital alopecia.

3. The method according to claim 1, wherein an extraction solvent for the milk thistle flower extract from which seeds have been removed is water, a $C_1$-$C_4$ lower alcohol, or a mixture thereof.

4. The method according to claim 1, wherein the composition promotes dermal papilla cell proliferation reduced due to senescence, and inhibits senescence of dermal papilla cells by inhibiting senescence-associated β-galactosidase activity and inhibiting production of senescence-associated secretory phenotypes, thereby activating dermal papilla cells.

5. The method according to claim 1, wherein the composition is a hair cosmetic composition selected from the group consisting of hair tonic, hair cream, hair lotion, hair shampoo, hair rinse, hair conditioner, hair spray, hair aerosol, pomade, powder, gel, sol-gel, emulsion, oil, wax, and aerosol.

* * * * *